(12) United States Patent
Fisher et al.

(10) Patent No.: US 12,263,106 B2
(45) Date of Patent: Apr. 1, 2025

(54) TRANSCATHETER IMPLANT DELIVERY DEVICE AND METHODS OF IMPLANT LOADING AND DELIVERY

(71) Applicant: Medtronic, Inc., Minneapolis, MN (US)

(72) Inventors: Alessandro Fisher, Santa Rosa, CA (US); Paulina Nguyen, Santa Rosa, CA (US); John Vucinich, Windsor, CA (US); Yas B. Neuberger, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 404 days.

(21) Appl. No.: 17/702,487

(22) Filed: Mar. 23, 2022

(65) Prior Publication Data
US 2022/0346992 A1 Nov. 3, 2022

Related U.S. Application Data

(60) Provisional application No. 63/183,097, filed on May 3, 2021.

(51) Int. Cl.
*A61F 2/95* (2013.01)
*A61F 2/24* (2006.01)
*A61F 2/97* (2013.01)

(52) U.S. Cl.
CPC .......... *A61F 2/9525* (2020.05); *A61F 2/2436* (2013.01); *A61F 2/97* (2013.01)

(58) Field of Classification Search
CPC .... A61F 2/9522; A61F 2/9524; A61F 2/9525; A61F 2/9526
See application file for complete search history.

(56) References Cited

U.S. PATENT DOCUMENTS

| | | | |
|---|---|---|---|
| 8,518,098 B2 | 8/2013 | Roeder et al. | |
| 9,199,348 B2 | 12/2015 | Creaven et al. | |
| 10,258,468 B2 | 4/2019 | Deem et al. | |
| 10,687,969 B2 | 6/2020 | Folan et al. | |
| 2008/0188928 A1* | 8/2008 | Salahieh | A61M 25/0054 623/2.11 |
| 2013/0231735 A1 | 9/2013 | Deem et al. | |
| 2014/0012369 A1 | 1/2014 | Murry, III et al. | |

(Continued)

FOREIGN PATENT DOCUMENTS

WO 2017/004209 A1 1/2017

OTHER PUBLICATIONS

Extended European Search Report, EP Application No. 22171079.1, dated Sep. 7, 2022.

*Primary Examiner* — Thomas McEvoy
(74) *Attorney, Agent, or Firm* — Medler Ferro Woodhouse & Mills PLLC

(57) ABSTRACT

Aspects of the disclosure are generally related to systems, devices and methods for transcatheter delivery and deployment of an implant, such as a prosthetic valve. Aspects of the disclosure include methods of loading the implant to the delivery device having a capsule assembly for sheathing the implant. The capsule assembly can include separable proximal and distal segments. Such methods of loading can include utilizing a collar and a funnel to guide the proximal segment over the implant and adjacent the distal segment to compress and fully sheathe the implant for delivery.

20 Claims, 9 Drawing Sheets

(56) References Cited

U.S. PATENT DOCUMENTS

| | | |
|---|---|---|
| 2014/0200649 A1 | 7/2014 | Essinger et al. |
| 2015/0374492 A1 | 12/2015 | Alkhatib |
| 2019/0008636 A1 | 1/2019 | Francis et al. |
| 2019/0224028 A1 | 7/2019 | Finn et al. |
| 2020/0069422 A1 | 3/2020 | Essinger et al. |
| 2020/0281719 A1* | 9/2020 | Keogh ................. A61F 2/2418 |

* cited by examiner

TRANSCATHETER IMPLANT DELIVERY DEVICE AND METHODS OF IMPLANT LOADING AND DELIVERY

CROSS-REFERENCE TO RELATED APPLICATIONS

This Non-Provisional patent application claims the benefit of the filing date of U.S. Provisional Patent Application Ser. No. 63/183,097, filed May 3, 2021, entitled "TRANSCATHETER IMPLANT Delivery DEVICE AND METHODS OF IMPLANT LOADING AND DELIVERY," the entire teachings of which are incorporated herein by reference.

FIELD

The present technology is generally related to systems, delivery devices and methods for transcatheter delivery and deployment of an implant, such as a prosthetic heart valve, including methods of loading the implant to the delivery device.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of a prosthetic heart valve or prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed condition within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place.

The present disclosure addresses problems and limitations associated with the related art.

SUMMARY

The techniques of this disclosure generally relate to systems and methods for transcatheter delivery and deployment of an implant or prosthesis, such as a prosthetic heart valve, to a defective heart valve. Aspects of the disclosure relate to methods of loading the implant onto the delivery device. Various aspects of the disclosure are particularly beneficial for transcatheter tricuspid repair as various delivery devices are configured to reduce the depth in which the device needs to be inserted into the right ventricle during delivery of the prosthesis. Access to a tricuspid valve can be challenging in that existing implanted devices may be in the anatomy, reducing the space available for the delivery device. Other implanted devices may also complicate the space available for the delivery device, increasing the potential for unwanted device interactions. In addition, visualization of the delivery system and implant may be challenging as metallic capsules can cause artifacts due to density. Further, chordae, papillary muscles serve as obstacles for delivery and the right ventricle is generally shorter than the left ventricle. All of these considerations result in a general desire for a system capable of delivering an implant to a tricuspid valve while reducing a length the delivery device extends into the right ventricle and past the valve annulus.

In one aspect, the present disclosure provides methods of loading an implant to a delivery device. Methods can include providing an implant having a distal end and a proximal end. Methods can include providing a proximal segment assembly including a catheter terminating at a proximal segment and further providing a distal segment assembly including a shaft connected to a distal segment. The shaft slidably being positioned within the catheter. Collectively, the proximal segment and the distal segment form or be part of a capsule assembly. The method further including coupling the implant to the shaft in that the distal end of the implant is within the distal segment and the proximal end of the implant is spaced from the proximal segment. Then, a collar is positioned adjacent a proximal end of the distal segment. A funnel is attached to the collar. The funnel extends over the proximal end of the implant. The method further includes at least partially positioning the funnel within the proximal segment. Then, the proximal segment is advanced over the funnel until the proximal segment is adjacent the collar. Next, the collar and the funnel are removed from the implant to provide a loaded, delivery device having the implant compressed and sheathed by the capsule assembly.

Such implant loading methods of the disclosure can provide numerous advantages. For one, during loading of a prosthetic heart valve, there is potential for reduced valve tissue damage compared to other methods of valve loading. A reduced risk of valve tissue damage can be achieved by applying a lubricious coating to the collar or manufacturing the funnel of a softer material such as a compliant silicone. Additionally, the valve loading steps and valve fixturing can be conducted by a single operator with ergonomic ease. The process simplicity will also minimize the amount of time required to train a new operator on the loading methods of the disclosure. Additionally, the present inventors have noticed that the loading methods of the disclosure may also prevent asymmetry in the prosthetic heart valve during loading due to the geometry of the collar. Implementing loading methods of the disclosure may also increase the ability of the operator to repeatedly load with consistent forces and loading time compared to other methods as there are only a few easy-to-conduct steps that are required to complete the valve loading process, which will minimize the room for operator error.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

As referred to herein, implants, stented prostheses, stented prosthetic heart valves or "prosthetic valves" useful with the various systems, devices and methods of the present disclosure may assume a wide variety of configurations. Stented prosthetic heart valves can include, for example, a bioprosthetic heart valve having tissue leaflets or a synthetic heart valve having polymeric, metallic or tissue-engineered leaflets, and can be specifically configured for replacing valves of the human heart. The prosthetic valves and stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., nitinol). The stent frame can be laser-cut from a single piece of material, or can be assembled from a number of discrete components.

Figure 1A:
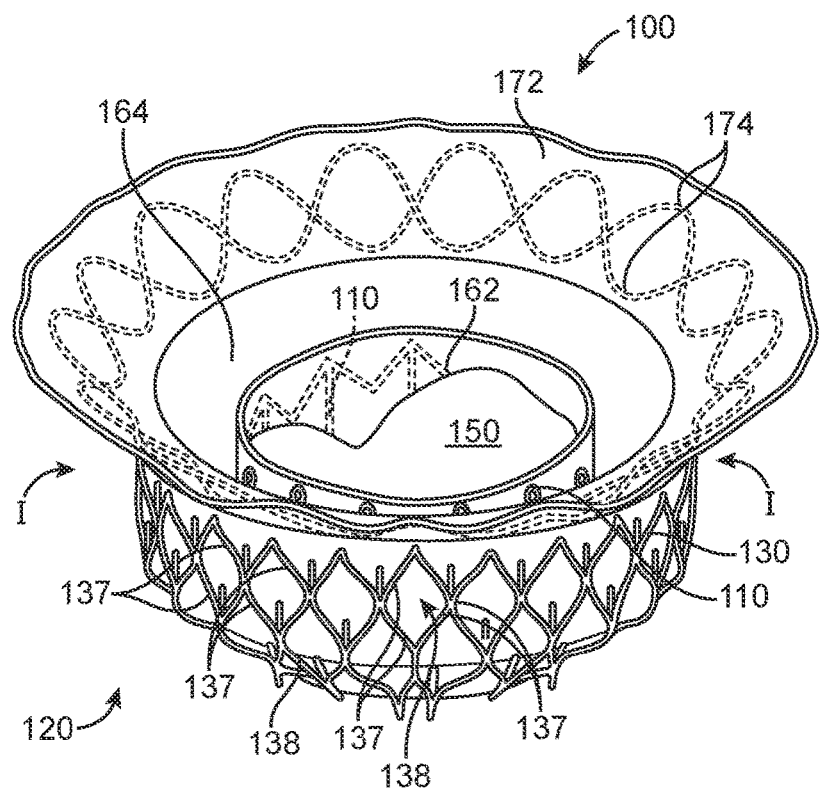
FIG. 1A is a top isometric view of a prosthetic heart valve in an expanded arrangement.
Figure 1B:
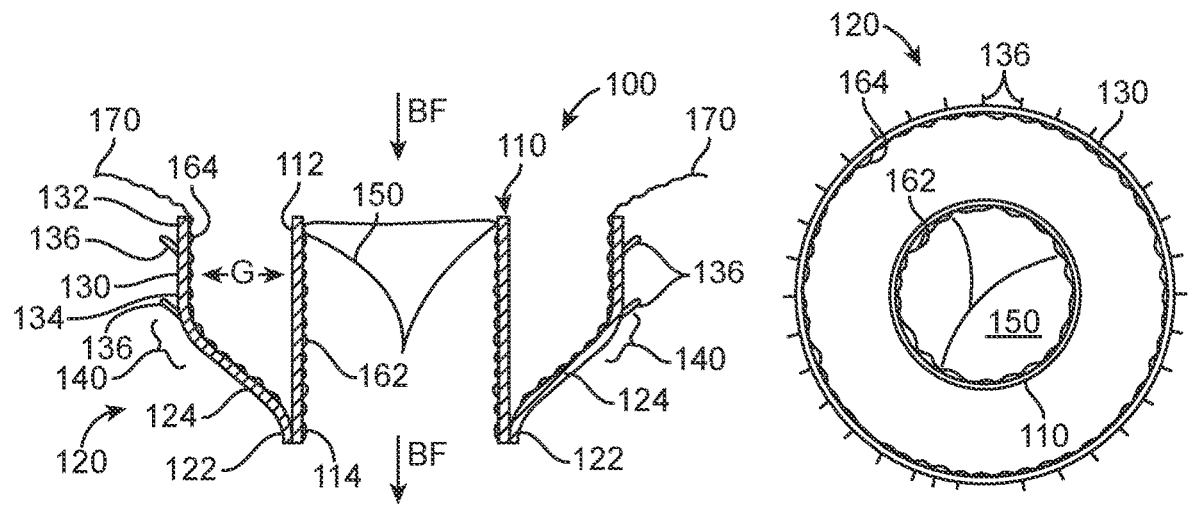
FIG. 1B is a cross-sectional side view of the prosthetic heart valve of FIG. 1A.
Figure 1C:
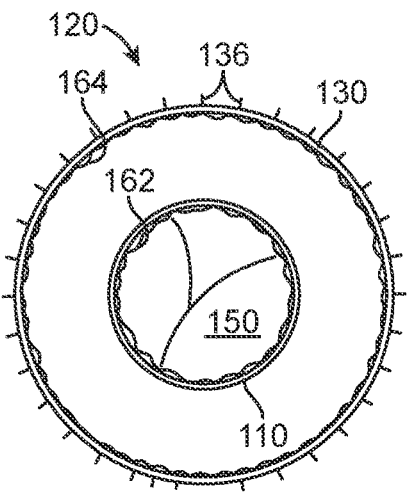
FIG. 1C is a top view schematically illustrating the prosthetic heart valve of FIGS. 1A-1B.

One non-limiting example of an implant, that being a stented prosthetic heart valve 100, is illustrated in FIGS. 1A-1C, The prosthetic heart valve 100 includes a valve support 110, an anchoring member 120 attached to the valve support 110, and a prosthetic valve assembly 150 within the valve support 110. Referring in particular to FIG. 1B, the valve support 110 has an inflow region 112 and an outflow region 114. The prosthetic valve assembly 150 is arranged within the valve support 110 to allow blood to flow from the inflow region 112 through the outflow region 114 (arrows BF), but prevent blood from flowing in a direction from the outflow region 114 through the inflow region 112.

The anchoring member 120 includes a base 122 attached to the outflow region 114 of the valve support 110 and a plurality of arms 124 projecting laterally outward from the base 122. The anchoring member 120 also includes a fixation structure 130 extending from the arms 124. The fixation structure 130 can include a first portion 132 and a second portion 134. The first portion 132 of the fixation structure 130, for example, can be an upstream region of the fixation structure 130 that, in a deployed configuration as shown in FIG. 1B, is spaced laterally outward apart from the inflow region 112 of the valve support 110 by a gap G. The second portion 134 of the fixation structure 130 can be a downstream-most portion of the fixation structure 130. The fixation structure 130 can be a cylindrical ring (e.g., straight cylinder or conical), and the outer surface of the fixation structure 130 can define an annular engagement surface configured to press outwardly against the native annulus. The fixation structure 130 can further include a plurality of fixation elements 136 that project radially outward and are inclined toward an upstream direction. The fixation elements 136, for example, can be barbs, hooks, or other elements that are inclined only in the upstream direction (e.g., a direction extending away from the downstream portion of the implant 100).

The anchoring member 120 has a smooth bend 140 between the arms 124 and the fixation structure 130. For example, the second portion 134 of the fixation structure 130 extends from the arms 124 at the smooth bend 140. The arms 124 and the fixation structure 130 can be formed integrally from a continuous strut or support element such that the smooth bend 140 is a bent portion of the continuous strut. In other examples, the smooth bend 140 can be a separate component with respect to either the arms 124 or the fixation structure 130. For example, the smooth bend 140 can be attached to the arms 124 and/or the fixation structure 130 using a weld, adhesive or other technique that forms a smooth connection. The smooth bend 140 is configured such that the implant 100 can be recaptured in a capsule or other container after the implant 100 has been at least partially deployed.

The implant 100 can further include a first sealing member 162 on the valve support 110 and a second sealing member 164 on the anchoring member 120. The first and second sealing members 162, 164 can be made from a flexible material, such as a polymeric material. The first sealing member 162 can cover the interior and/or exterior surfaces of the valve support 110. The first sealing member 162 is attached to the interior surface of the valve support 110, and the prosthetic valve assembly 150 is attached to the first sealing member 162 and commissure portions of the valve support 110. The second sealing member 164 is attached to the inner surface of the anchoring member 120. As a result, the outer annular engagement surface of the fixation structure 130 is not covered by the second sealing member 164 so that the outer annular engagement surface of the fixation structure 130 directly contacts the tissue of the native annulus.

The implant 100 can further include an extension member or brim 170. The extension member 170 can be an extension of the second sealing member 164, or it can be a separate component attached to the second sealing member 164 and/or the first portion 132 of the fixation structure 130. The extension member 170 can be a flexible member that, in a deployed state as shown in FIGS. 1A-1B, flexes relative to the first portion 132 of the fixation structure 130. In operation, the extension member 170 guides the implant 100 during implantation such that the device is located at a desired elevation and centered relative to the native annulus. In some embodiments, one or more components of the extension member 170 can be made of or include a radiopaque material.

As best shown in FIG. 1A, valve support 110 defines a first frame (e.g., an inner frame) and fixation structure 130 of the anchoring member 120 defines a second frame (e.g., an outer frame) that each include a plurality of structural elements. The fixation structure 130, more specifically, includes structural elements 137 arranged in diamond-shaped cells 138 that together form at least a substantially cylindrical ring when freely and fully expanded as shown in FIG. 1A. The structural elements 137 can be struts or other structural features formed from metal, polymers, or other suitable materials that can self-expand or be expanded by a balloon or other type of mechanical expander.

The fixation structure 130 can be a generally cylindrical fixation ring having an outwardly facing engagement surface. For example, in the embodiment shown in FIG. 1A, the outer surfaces of the structural elements 137 define an annular engagement surface configured to press outwardly against the native annulus in the deployed state. In a fully expanded state without any restrictions, the fixation structure 130 is at least substantially parallel to the valve support 110. However, the fixation structure 130 can flex inwardly (arrow I) in the deployed state when it presses radially outwardly against the inner surface of the native annulus of a heart valve.

The first sealing member 162 lines the interior surface of the valve support 110, and the second sealing member 164 along the inner surface of the fixation structure 130. The extension member 170 has a flexible web 172 (e.g., a fabric) and a support member 174 (e.g., metal or polymeric strands) attached to the flexible web 172. The flexible web 172 can extend from the second sealing member 164 without a metal-to-metal connection between the fixation structure 130 and the support member 174. For example, the extension member 170 can be a continuation of the material of the second sealing member 164. Several embodiments of the extension member 170 are thus a floppy structure that can readily flex with respect to the fixation structure 130. The support member 174 can have a variety of configurations and be made from a variety of materials, such as a double-serpentine structure made from Nitinol. Additional details regarding the implant 100 can be found in U.S. patent Ser. No. 15/643,011, the disclosure of which is hereby incorporated by reference.

Figure 2:
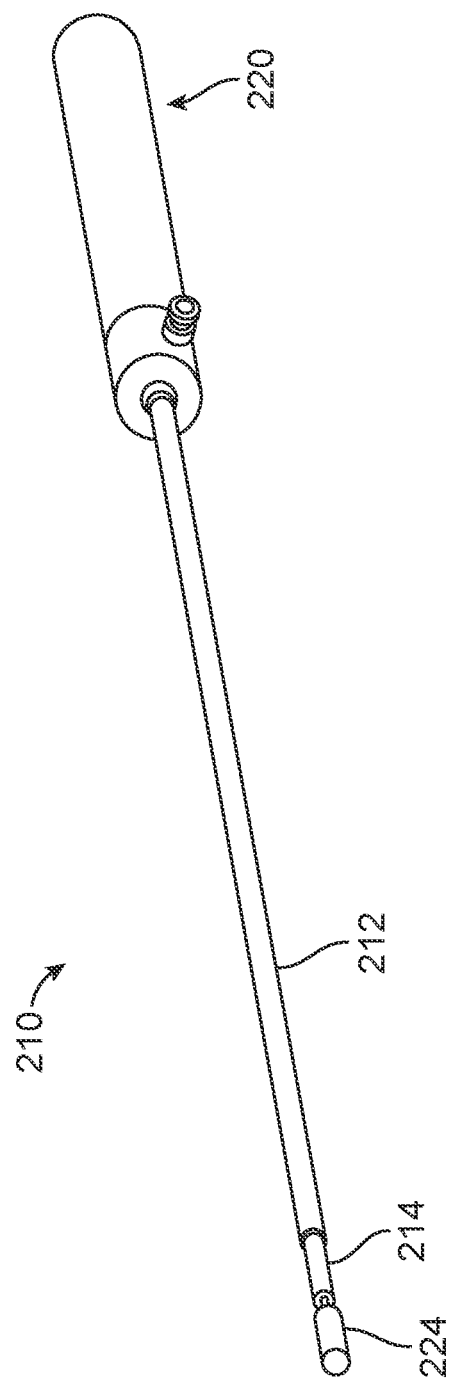
FIG. 2 is a perspective view of a delivery device suitable for delivering the prosthetic heart valve of FIGS. 1A-1C.
Figure 3:
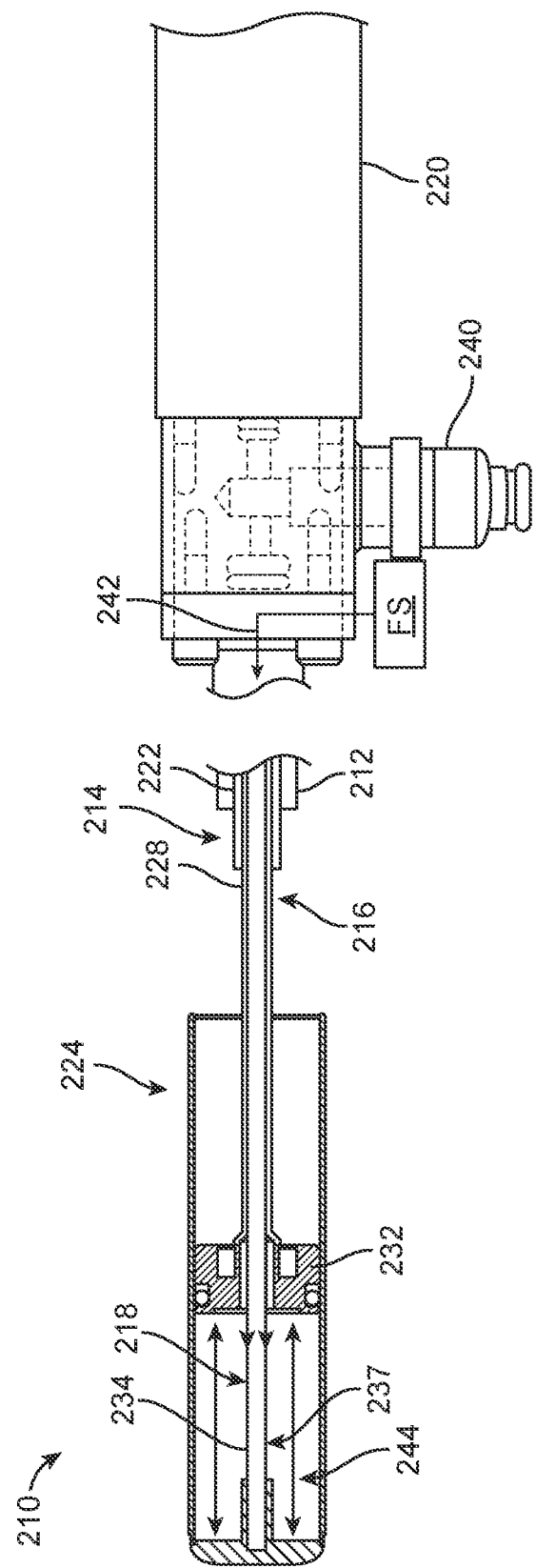
FIG. 3 is a schematic, cross-sectional illustration of select components of the delivery device of FIG. 2.
Figure 4:
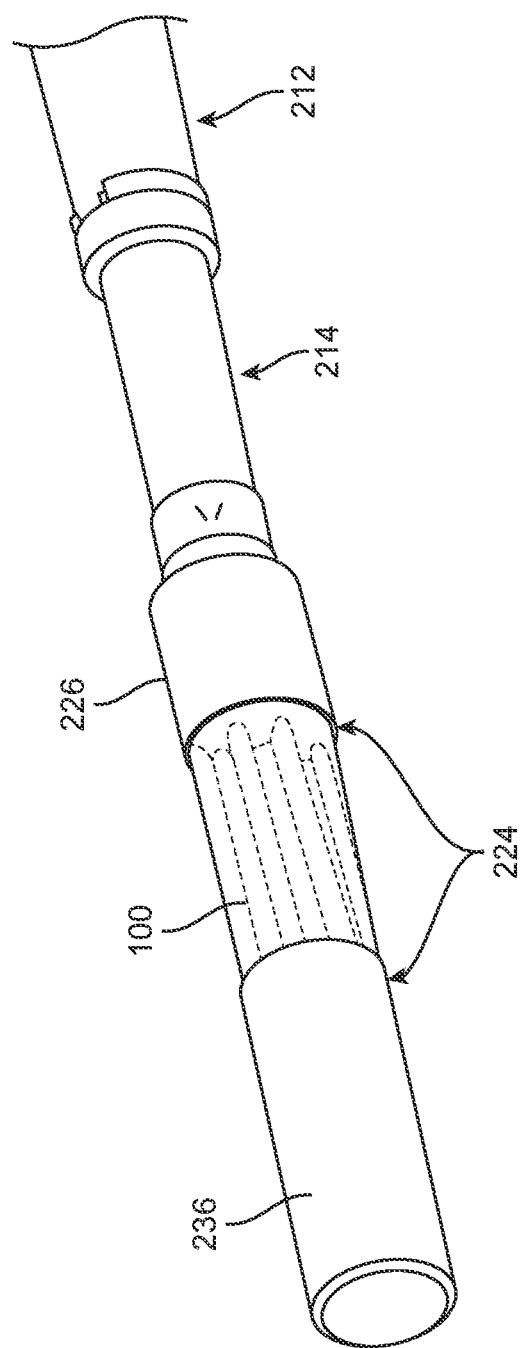
FIG. 4 is a perspective view of a distal end of the delivery device of FIGS. 2-3 including a capsule assembly.
Figure 5A:
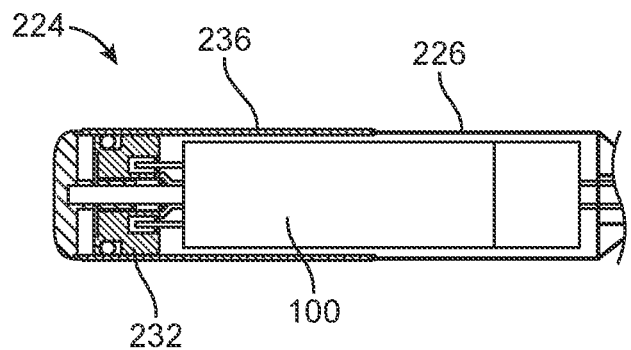
FIG. 5A is a schematic, cross-sectional view of the capsule assembly of FIG. 4 in a loaded arrangement.
Figure 5B:
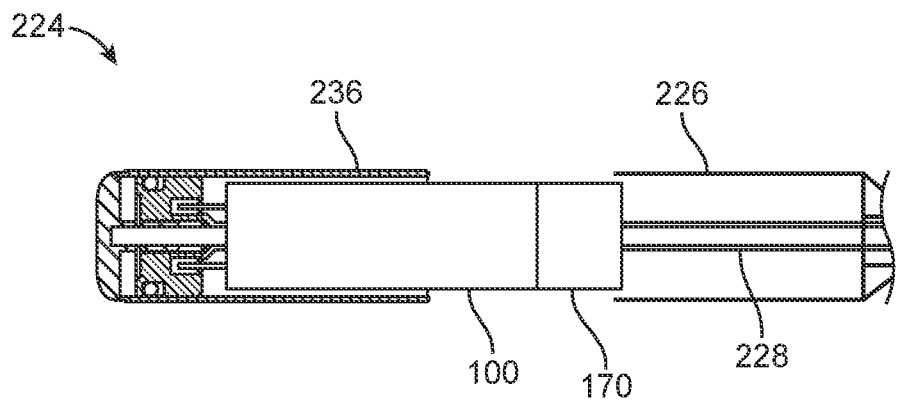
FIGS. 5B-5C are a schematic, cross sectional views of the capsule assembly of FIGS. 4-5A in a partially, deployed arrangement.
Figure 5C:
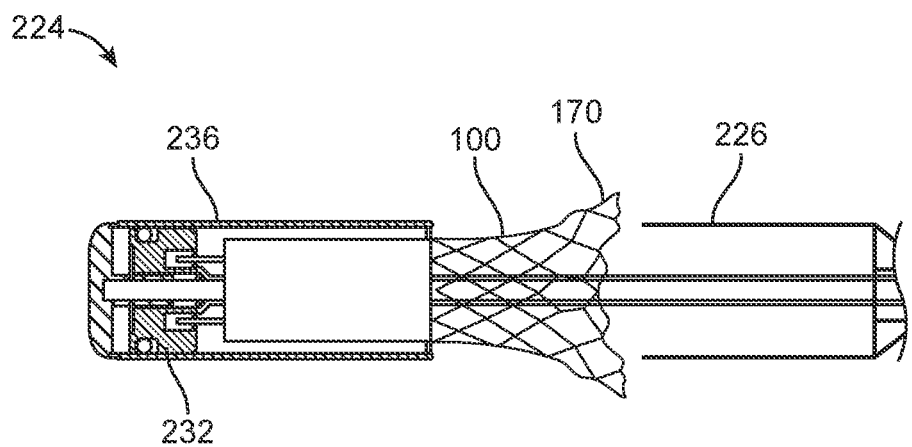

A delivery device for transcatheter delivery of an implant of the disclosure, such as implant of FIGS. 1A-1C is collectively shown in FIGS. 2-3. In general terms, the delivery device 210 is arranged and configured for percutaneously delivering a stented prosthetic heart valve 100 or other implant or prosthesis to a patient's native defective heart valve or other portion of a patient's anatomy via transcatheter delivery. Generally, the delivery device 210 includes an optional outer sheath 212, a proximal segment assembly 214, a valve retaining assembly 216, a distal segment assembly 218 and a handle assembly 220. The proximal segment assembly 214 includes a catheter 222. The valve retaining assembly 216 includes a catheter 228 that supports a piston/valve retainer 232. The piston/valve retainer 232 can be of any type known in the art for releasably maintaining a prosthesis or implant on a delivery device for transcatheter delivery. The valve retaining assembly 216 is slidably positioned at least partially within the proximal segment assembly 214. The distal segment assembly 218 includes a shaft 234 having a distal end 237 that supports a capsule or capsule assembly 224. The shaft 234 is slidably positioned at least partially within the catheter 228 and may optionally be hollow for defining a hydraulic fluid path, for example. The delivery device 210 provides a loaded, compressed arrangement in which the implant 100 compressively retained on the piston/valve retainer 232 and entirely within the capsule 224. Once loaded and compressed, the implant 100 is located at a target site, the implant 100 is unsheathed from the capsule 224 and is released from the piston/valve retainer 232 to permit the prosthetic valve 100 to self-expand to an expanded arrangement as shown in FIG. 1A.

Movement of any of components 212, 214, 216 and 218, among others, can be actuated with the handle assembly 220. In one non-limiting example, movement of one or more components is achieved with hydraulics. In such an example, the handle assembly 220 can be connected to a fluid source FS (FIG. 3) at port 240. Optionally, the fluid source FS may be fluidly connected to a fluid path 242 extending through the shaft 234 to a cavity 244 in the capsule 224 to actuate distal advancement of the capsule 224 in effort to free the implant, allowing the implant to release from the piston/valve retainer 232, fully deploying the implant 100.

In various embodiments of the disclosure, the capsule 224 is an assembly including a proximal portion 226 and a distal segment 236 as shown in FIGS. 4-9D. In one example, the distal segment 236 and the proximal segment 226 may be abutting in the compressed arrangement (FIG. 6A). In one example, to unsheathe the prosthetic valve 100, the distal segment 236 can be distally advanced via movement of the shaft 218 via the handle assembly 220, the proximal segment 226 can be proximally withdrawn via proximal movement of the catheter 222 with the handle assembly 220 or a combination of moving both the proximal and distal segments 226, 236.

Figure 6A:
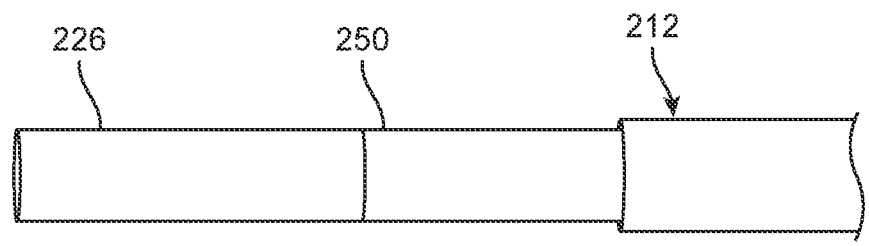
FIGS. 6A-6B are partial, side views of a recapture funnel that can be incorporated into the delivery device of FIGS. 2-3.
Figure 6B:
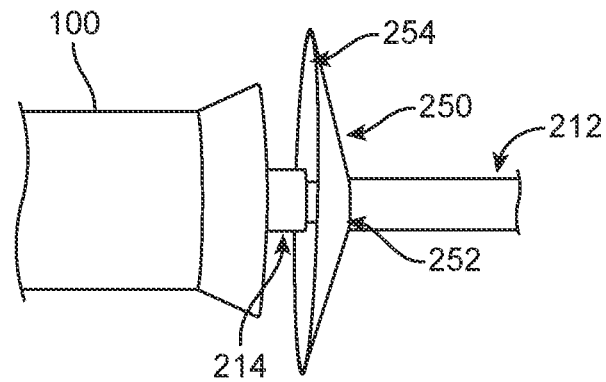
Figure 7:
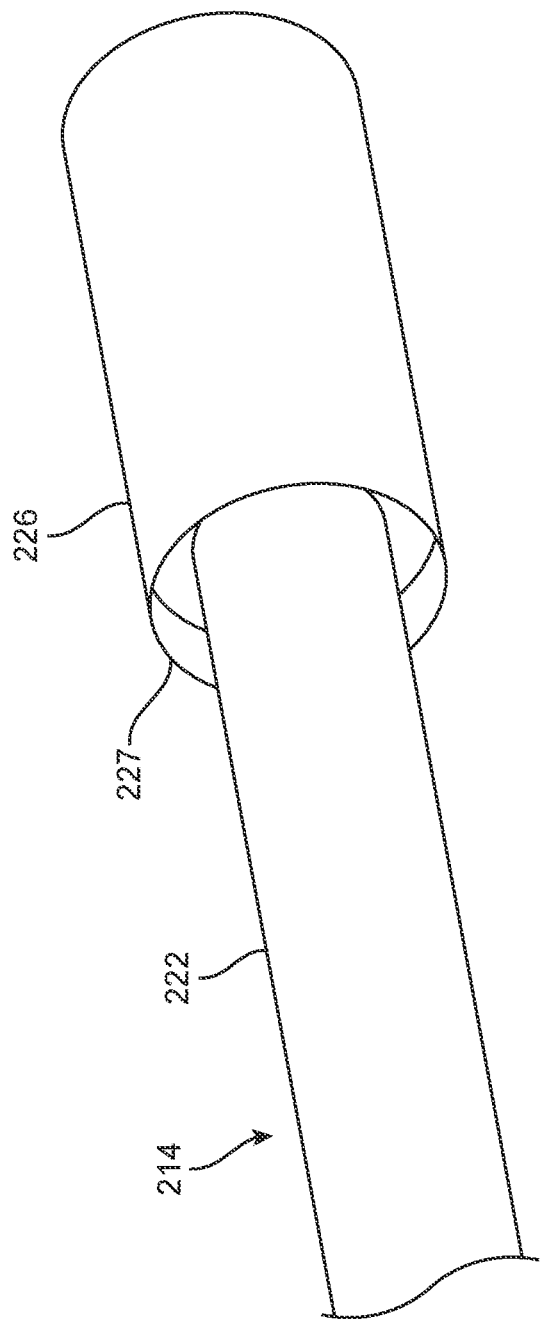
FIG. 7 is a partial, perspective view of a proximal section of the capsule assembly of FIG. 4 illustrating an overhang in which the recapture funnel of FIGS. 6A-6B can be maintained during delivery of the implant.
Figure 8A:
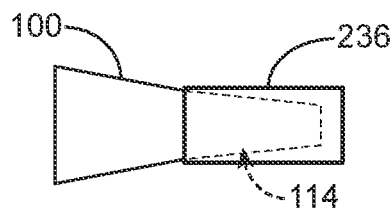
FIGS. 8A-8E are schematic illustrations of a method of loading the implant within the capsule assembly of FIGS. 4-5C.
Figure 8B:
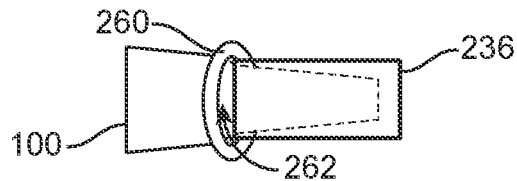
Figure 8C:
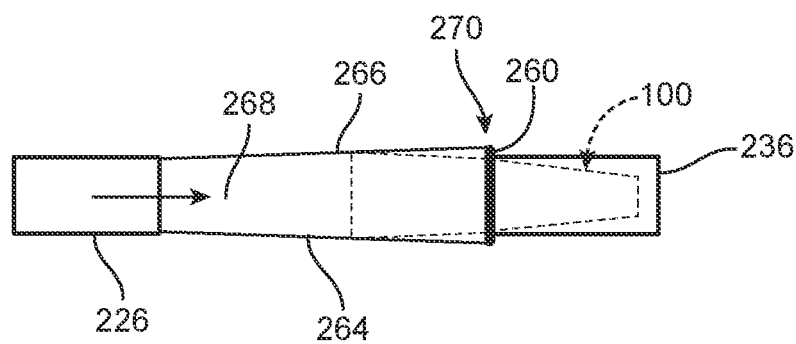
Figure 8D:
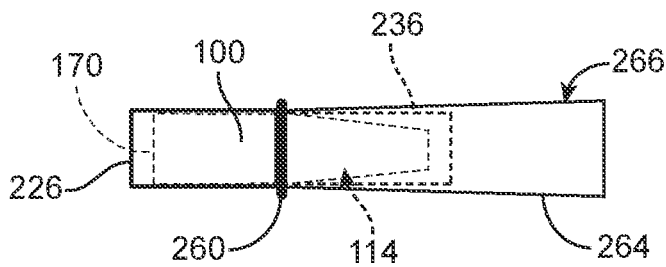
Figure 8E:
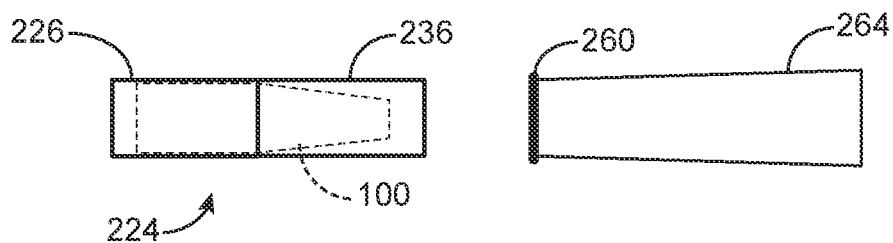
Figure 9A:
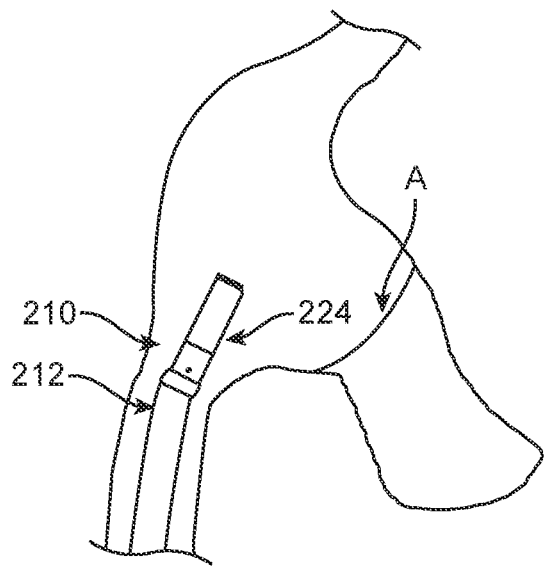
FIGS. 9A-9D are schematic illustrations of a method of delivering the implant to a tricuspid valve annulus.
Figure 9B:
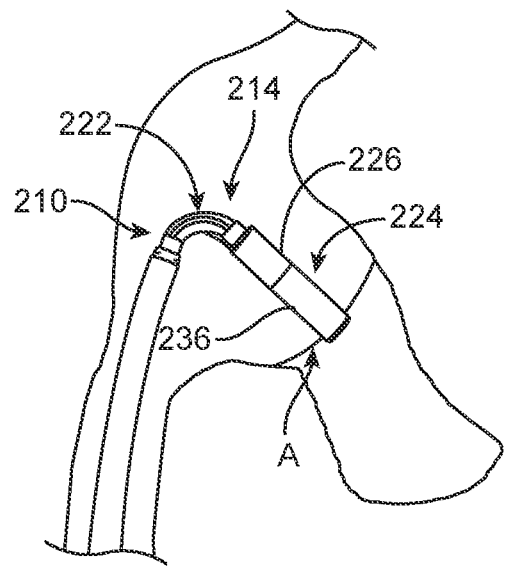
Figure 9C:
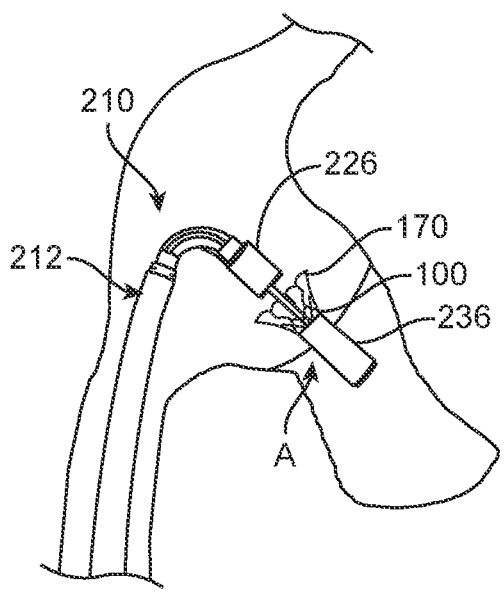
Figure 9D:
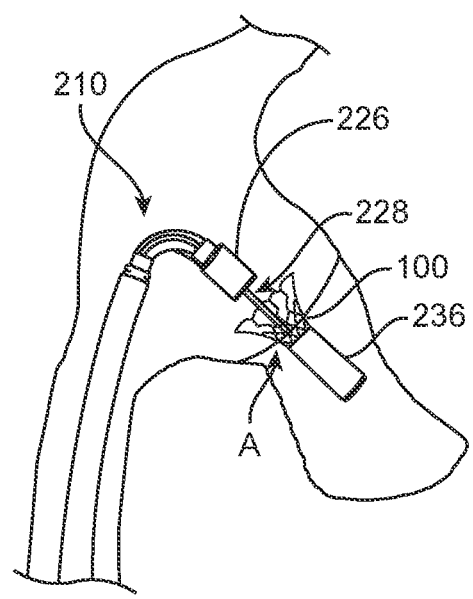

With additional reference to FIGS. 6A-7, the delivery device 210 can optionally include a recapture funnel 250. In one example, a proximal end 252 of the recapture funnel 250 is secured to a distal end of the outer sheath 212. During loading of the implant 100, the recapture funnel 250 tucks into an overhang 227 on the proximal end of the proximal segment 226 to provide atraumatic tracking of the delivery device (FIG. 6A). When the outer sheath 212 is retracted and/or the catheter 222 is distally advanced out of the outer sheath 212, the recapture funnel 250 is released from the overhang 227 and transitions to a deployed arrangement in which a distal end 254 of the funnel 250 flares outwardly with respect to the proximal end 252 of the funnel 250, which is secured to the outer sheath 212 (FIG. 6B). If desired, a partially-deployed implant 100 can be recaptured by pulling the implant 100 over the proximal segment 226 and into the recapture funnel 250. The funnel 250 and implant can then be retracted into the outer sheath 212 to compress the implant for repositioning.

Referring in addition to FIGS. 8A-8E, one method of loading the stented prosthesis 100 to the delivery device 210 is generally depicted. The method is schematically illustrated and not all of the delivery device 210 components are shown for ease of illustration. In one loading method example, the implant or prosthetic valve 100 is loaded into onto the piston 232 and compressed around the catheter 228 using any known procedure for crimping an implant onto a delivery device for transcatheter delivery (see, FIGS. 5A-5B). At this stage the proximal and distal segments 226, 236 of the capsule assembly 224 are separated, spaced apart and not abutting. The outflow region 114 (i.e. distal end) of the implant 100 is partially positioned within the distal segment 236 and the proximal end (i.e. inflow region 112 and/or brim 170) of the implant 100 extends outside of the distal segment 236. In some embodiments, the implant 100 is biased to naturally expand and in such examples, the proximal end 112/170 of the implant 100 may be at least partially expanded are compared to the distal end 114. A collar 260 is provided. In one example, the collar 260 is a ring defining a circular aperture 262. The collar 260 can be positioned at a proximal end of the distal segment 236. The collar 260 may be distally advanced over the implant 100 or can alternatively be advanced over the implant proximally, from a position starting over the distal segment 236. In yet another example, the collar 260 may be already positioned over the implant 100 at the time when the distal end 114 of the implant 100 is being inserted within the distal segment 236. A loading funnel 264 is provided and is secured to the collar 260 such that the loading funnel 264 sheathes at least a portion of the implant 100 between the distal segment 236 and the proximal segment 226. The collar 260 can optionally include a lip (not shown) or other features for engaging the loading funnel 264 or the funnel 264 can be maintained on the collar 260 via a force fit. The loading funnel 264 is configured to slightly compress the proximal portion of the implant 100, which is outside of the capsule assembly 224. In one example, the loading funnel 264 is made of a material that is compliant. In one example, the loading funnel 264 is at least partially made of nylon, compliant silicone or other compliant polymer. A proximal end 266 of the loading funnel 264 is tucked into the proximal segment 226 and defines a ramped surface 268 that flares outwardly in a direction of the collar 260. The ramped surface 268 can include a lubricious coating or naturally lubricious coating (not visible) in some examples. The ramped surface 268 allows the proximal segment 226 to be distally advanced in the direction of the distal segment 236 to bring the capsule segments 226, 236 together, compressively sheathing the implant 100 within the capsule assembly 224 (formed by segments 226, 236). Once the implant 100 is fully loaded within the capsule assembly 224, the collar 260 and loading funnel 264 can be removed from the delivery device 210. In one example, the loading funnel 264 is mechanically pulled out of the proximal segment 226 so that it is inverted over the distal segment 236 and the collar 260 is mechanically pulled away from the implant 100 and over and off of the distal segment 236.

The aforementioned implant loading method provides numerous advantages. First, during loading of a prosthetic heart valve, there is potential for reduced valve tissue damage compared to other methods of valve loading. A reduced risk of valve tissue damage can be achieved by applying the lubricious coating to the collar or manufacturing the funnel of a softer material such as silicone or other soft plastics, or a flexible fabric that will not cause abrasion to the implant frame. Additionally, the valve loading steps and valve fixturing can be conducted by a single operator to perform the valve loading procedure with ergonomic ease. The process simplicity will also minimize the amount of time required to train a new operator on the loading methods of the disclosure. Additionally, the present inventors have noticed that the loading methods of the disclosure may also prevent asymmetry in the valve during loading due to the geometry of the collar. Implementing loading methods of the disclosure may also increase the ability of the operator to repeatably load with consistent forces and loading time compared to other methods as there are only a few easy-to-conduct steps that are required to complete the valve loading process, which will minimize the room for operator error.

In various methods of the disclosure the implant 100 is loaded onto the delivery device 210 in the loaded arrangement, compressed and fully sheathed by the capsule assembly 224 so that the distal segment 236 abuts the proximal segment 226. Referring now in addition to FIGS. 9A-9D, the delivery device 210 is directed through a patient's femoral vein to the inferior vena cava IVC. The delivery device 210 is advanced and articulated to orient the capsule assembly 224 toward the valve annulus A to be treated. In one example, the annulus A is a tricuspid valve annulus. Once the capsule assembly 224 is at the valve annulus A, the proximal segment assembly 226 is held in place as the distal segment 236 and valve retainer assembly (see also FIG. 3) are advanced through the valve annulus A, leaving the proximal segment 226 at least partially within the right atrium RA. In some examples, the proximal segment 226 is entirely within the right atrium RA or proximal to the valve annulus A as the distal segment 236 is advanced. In this way, only the distal segment 236 is advanced through the valve annulus A, which results in a shorter portion of the device 210 extending through the annulus A as compared to a method in which an entire capsule or capsule assembly is inserted through the annulus A. Reducing the depth at which the delivery device 210 enters the right ventricle RV increases the patient population that can benefit from delivery devices of the disclosure. As the distal segment 236 and the piston 232 are lowered toward the right ventricle RV, the brim 170 of the implant 100 becomes exposed within the right atrium RA as the proximal and distal segments 226, 236 are no longer abutting and fully sheathing the implant 100. Optionally, the catheter 222 can be retracted proximally if additional space is needed to expose the brim 170 or implant 100 in the right atrium RA. In some methods, the shaft 234 (within 228) secured to the distal segment 236 can be used to adjust and position the distal segment 236 in the annulus A. In some methods, hydraulics are utilized to adjust movement of the distal segment 236. Optionally, the recapture funnel 270 and outer sheath 212 can be utilized to recapture the implant 100 prior to the implant being fully deployed from the delivery device 210. Once in the desired position, the implant 100 is deployed from the delivery device 210. The method of deploying the implant from the delivery device can be of any known method of disengaging a prosthetic valve or implant from a shaft or piston. Then, the distal segment 236 can be proximally drawn through the implant 100 and the delivery device 210 can be proximally withdrawn from the patient in the same manner in which it was delivered.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of loading an implant to a delivery device, the method comprising:
    loading a distal end of an implant into a distal segment of a capsule assembly of the delivery device such that a proximal end of the implant is proximal of the distal segment and the proximal end of the implant is spaced from a distal end of a proximal segment of the capsule assembly;
    positioning a collar adjacent a proximal end of the distal segment;
    positioning a funnel such that a distal end of the funnel is disposed adjacent to the collar, the funnel extending over the proximal end of the implant and at least partially positioning the funnel within the proximal segment;
    advancing the proximal segment towards the distal segment until the distal end of the proximal segment is adjacent the collar, the proximal end of the implant is radially compressed within the proximal segment, and the funnel is disposed over the distal segment; and
    removing the collar and the funnel from the delivery device.

2. The method of claim 1, wherein the implant is a prosthetic heart valve.

3. The method of claim 1, wherein the funnel includes a lubricious coating.

4. The method of claim 1, wherein positioning the collar adjacent the proximal end of the distal segment comprising advancing the collar over the distal segment proximally toward the implant.

5. The method of claim 1, wherein positioning the collar adjacent the proximal end of the distal segment comprises positioning the collar over the proximal end of the implant and distally advancing the collar distally over the implant.

6. The method of claim 1, wherein the collar defines a circular opening.

7. The method of claim 1, wherein the funnel compresses the implant as the proximal segment is advanced towards the distal segment.

8. The method of claim 1, wherein the funnel defines a ramped surface.

9. The method of claim 8, wherein prior to advancing the proximal segment, the ramped surface of the funnel flares outwardly in a direction of the distal segment.

10. The method of claim 1, wherein removing the collar and the funnel from the delivery device comprises distally advancing the collar over the distal segment.

11. The method of claim 1, wherein removing the collar and the funnel from the delivery device comprises distally advancing the funnel over the distal segment.

12. The method of claim 1, wherein after removing the collar and the funnel from the delivery device, the proximal segment and the distal segment are moved together so that the proximal segment contacts the distal segment.

13. The method of claim 1, wherein the funnel is compliant.

14. The method of claim 1, wherein the delivery device further comprises a shaft coupled to the distal segment, wherein loading a distal end of the implant into the distal segment comprises positioning the implant over the shaft.

15. The method of claim 14, wherein the collar is positioned adjacent the proximal end of the distal segment as the implant is positioned on the shaft.

16. The method of claim 14, wherein the collar is positioned adjacent the proximal end of the distal segment after the implant is positioned on the shaft.

17. The method of claim 14, wherein the shaft includes a piston, and wherein loading the implant into the distal segment comprises compressing the implant onto the piston.

18. The method of claim 14, wherein the shaft is hollow.

19. The method of claim 1, wherein positioning the collar adjacent the proximal end of the distal segment comprises positioning the collar on an exposed portion of the implant proximal of the proximal end of the distal segment such that the collar compresses the exposed portion of the implant.

20. A method of loading an implant to a delivery device, the method comprising:
    loading a distal end of an implant into a distal segment of a capsule assembly of the delivery device such that a proximal end of the implant is proximal of the distal segment and the proximal end of the implant is spaced from a distal end of a proximal segment of the capsule assembly;
    positioning a collar adjacent a proximal end of the distal segment by proximally advancing the collar over the distal segment or advancing the collar over the implant;
    positioning a funnel such that a distal end of the funnel is disposed adjacent to the collar, the funnel extending over the proximal end of the implant and at least partially positioning the funnel within the proximal segment;
    advancing the proximal segment towards the distal segment until the distal end of the proximal segment is adjacent the collar and the proximal end of the implant is radially compressed within the proximal segment; and removing the collar and the funnel from the delivery device.

* * * * *